United States Patent [19]
Tomaskovic et al.

[11] Patent Number: 5,866,750
[45] Date of Patent: Feb. 2, 1999

[54] METHOD FOR REMOVAL OF METAL ALKOXIDE COMPOUNDS FROM LIQUID HYDROCARBON

[75] Inventors: Robert Stephen Tomaskovic, Houston; Michael Wayne Potter, Sugar Land; William Charles Malven, Houston, all of Tex.

[73] Assignee: Union Carbide Chemicals & Plastics Technology Corporation, Danbury, Conn.

[21] Appl. No.: 548,291

[22] Filed: Nov. 1, 1995

[51] Int. Cl.⁶ .............................. C07C 7/00; C07C 7/10; C10G 17/00; B01D 11/00
[52] U.S. Cl. .......................... 585/853; 585/833; 585/854; 585/858; 585/868; 208/252; 208/253; 423/63; 423/64; 423/82; 423/84
[58] Field of Search ...................... 585/833, 853, 585/854, 858, 868; 208/252, 253; 423/63, 64, 82, 84

[56] References Cited

U.S. PATENT DOCUMENTS

| | | | |
|---|---|---|---|
| 3,477,813 | 11/1969 | Fernald et al. | 23/143 |
| 3,644,321 | 2/1972 | Koga et al. | 260/93.7 |
| 3,904,498 | 9/1975 | Hesse et al. | 204/157.1 S |
| 4,016,349 | 4/1977 | McKenna | 528/482 |
| 4,018,867 | 4/1977 | Lee | 423/115 |
| 4,522,702 | 6/1985 | Kukes et al. | 208/252 |
| 4,911,758 | 3/1990 | Lin et al. | 106/89 |
| 4,940,833 | 7/1990 | Drake et al. | 585/868 |
| 5,242,549 | 9/1993 | Potter et al. | 203/6 |
| 5,245,007 | 9/1993 | Yamamoto et al. | 528/483 |
| 5,270,443 | 12/1993 | Magni et al. | 528/485 |

FOREIGN PATENT DOCUMENTS 947111  1/1964  United Kingdom .

*Primary Examiner*—Glenn Caldarola
*Assistant Examiner*—In Suk Bullock
*Attorney, Agent, or Firm*—P. A. Doody

[57] ABSTRACT

A method for recovering titanium and vanadium compounds, such as alkoxides, from a liquid hydrocarbon mixture by hydrolyzing the mixture with a base or acid wash having a sufficiently different density so that two liquid phases form, and separating the two liquid phases.

14 Claims, No Drawings

– 5,866,750 –

METHOD FOR REMOVAL OF METAL ALKOXIDE COMPOUNDS FROM LIQUID HYDROCARBON

FIELD OF THE INVENTION

This invention relates to the separation and partial recovery of components of a complex mixture of organic compounds and inorganic compounds. More particularly, the invention relates to a process for the separation of titanium and vanadium alkoxide compounds from solutions of liquid hydrocarbons, such as those resulting from the preparation of an olefin polymerization catalyst precursor.

BACKGROUND OF THE INVENTION

The polymerization of lower α-olefins to produce thermoplastic polymers is an industry of substantial commercial importance. The polymeric products of such a process, e.g., polypropylene, polyethylene and ethylene/propylene copolymers, are important materials of commerce because of the relatively low cost of the polymers and the desirable properties they possess. The polymerization of ethylene is relatively uncomplicated because the polyethylene polymer exists in only one steric form. Higher α-olefins such as propylene form polymers of several steric types because of the pendant alkyl group of the olefin monomer. The cost and value of polypropylene, for example, will be greatly influenced by the steric form in which the polymer is produced. Most commercial polypropylene is crystalline and highly stereoregular and is usually isotactic. Polypropylene which is not stereoregular is termed atactic and is not crystalline. This amorphous polymer is less desirable and, if present in substantial quantities, must usually be removed as by extraction before the polypropylene will have commercially attractive properties. In recent commercial polypropylene production, it is virtually mandatory for economic reasons to employ polymerization catalyst which is sufficiently active and produces a highly stereoregular product so that polypropylene of acceptable properties will be produced without the need for extraction or deashing steps.

The production of such an active, stereoregular catalyst is frequently a rather complicated process with much of the complexity being encountered during the production of what is conventionally termed the olefin polymerization procatalyst. This catalyst precursor is frequently a titanium-containing solid and often contains moieties of magnesium and halide, particularly chloride. For polyethylene production, the procatalyst is frequently a vanadium-containing solid. Such procatalysts are described in numerous patents and other references and vary in chemical character, depending upon the particular catalyst desired. One class of procatalyst results from the reaction of a magnesium compound, often a magnesium alkoxide compound, with a tetravalent titanium halide in the presence of a halohydrocarbon reaction diluent and an electron donor which is often an alkyl ester of an aromatic monocarboxylic or dicarboxylic acid.

The procatalyst is generally a solid material and is easily separated from the media of its production. The remaining waste product is a liquid material and contains at least some of unreacted heavy metal halide, halohydrocarbon, e.g., chlorobenzene, unreacted electron donor, and a wide array of haloalkoxide compounds or complexes thereof with other chloroalkoxide compounds or aromatic esters.

This waste product from such procatalyst production presents a substantial disposal problem which also adversely affects the economy of the polymerization process. It is an advantage to be able to separate the components of such a waste stream and to recover for reuse the more valuable components of the product such as titanium tetrachloride and the halohydrocarbon reaction diluent.

One such method of component separation is described by Potter et al., U.S. Pat. No. 5,242,549. This references provides for the separation of waste product components by a method wherein a separation solvent is added to the waste product, and the liquid components are separated by distillation. The resulting waste stream of that patent comprises titanium compounds, such as titanium alkoxides and chloroalkoxides and complexes thereof, dissolved in the separation solvent. The separation solvent is typically an aromatic halohydrocarbon such as chlorobenzenes and chlorotoluenes. A great economic advantage would be realized if the metal compounds could be removed from the separation solvent as solids for disposal, and the separation solvent further purified to be reused in the distillation process.

SUMMARY OF INVENTION

This invention presents a novel method for the separation and recovery of titanium and vanadium alkoxide compounds from a liquid hydrocarbon mixture. In one embodiment of this invention, the hydrocarbon mixture is hydrolyzed using an aqueous base solution having a density higher than the density of the liquid hydrocarbon, so that the metal compounds concentrate into the aqueous base solution as hydroxides, and a two liquid phase system forms. The lower phase comprises the basic solution with the metal hydroxide, and the upper phase is the substantially metal-free liquid hydrocarbon. The two phases are separated with the hydrocarbon phase being further purified as needed.

In another embodiment of this invention, the metal alkoxide compounds comprise titanium or vanadium alkoxides or chloroalkoxides.

In another embodiment of this invention, the hydrocarbon is a chlorohydrocarbon such as dichlorobenzene or chlorotoluene, or the hydrocarbon is xylene.

In still another embodiment of this invention, the liquid hydrocarbon mixture is hydrolyzed with an acidic solution, so that the heavy metal concentrates into the acidic solution and a two-phase mixture forms. The two phases are then separated with the liquid hydrocarbon being further purified as needed.

DETAILED DESCRIPTION OF THE INVENTION

The process of the invention comprises the separation and recovery of heavy metal alkoxide compounds, such as titanium alkoxides or vanadium alkoxides, from a liquid hydrocarbon solution, followed by further distillation or other purification of the liquid hydrocarbon. Although the process is broadly applicable to separation of such a mixture independent of its origin, the process is particularly applicable to the removal of excess titanium alkoxide compounds from a separation solvent waste product stream such as described in U.S. Pat. No. 5,242,549. That patent describes a waste product stream (stream 22 in that patent) comprised of titanium alkoxide and titanium chloroalkoxide compounds and a separation solvent of dichlorobenzene, chlorotoluene, or xylene. Utilizing the present invention, such a waste stream can be treated to remove the titanium compounds, and purify the liquid hydrocarbon for reuse in the system.

The stream undergoing treatment by the process of the present invention is a mixture of compounds of titanium or vanadium, particularly alkoxides and chloroalkoxides of those metals, in a liquid hydrocarbon. The solution may also contain various complexes of metal alkoxy compounds with other metal alkoxy compounds or with aromatic esters. The liquid hydrocarbon may be any useful separation solvent such as halohydrocarbons or aromatics, such as xylene. Typical separation solvents are described in U.S. Pat. No. 5,242,549. The disposal of such a waste product poses environmental hazards and represents a considerable economic detriment to the overall olefin polymerization process. The recovery of the liquid hydrocarbon for reuse in the overall olefin polymerization procatalyst production is of substantial economic benefit. Further, the recovery of solid titanium and vanadium compounds for further treatment or disposal also provides substantial benefit to the procatalyst production process.

The process of the invention involves the hydrolysis phase, and the separation and removal of the metal compounds, optionally followed by further purification of the liquid hydrocarbon to remove other impurities. The hydrolysis may be accomplished by either a basic wash or an acid wash, with a base wash being the preferred embodiment. Distillation or other purification of the liquid hydrocarbon may be carried out by any conventional means.

The purified liquid hydrocarbon stream may then be re-used in the system that originally generated the waste stream. For instance, if the present invention is used to treat waste stream 22 from U.S. Pat. No. 5,242,549, then the purified hydrocarbon may be recycled as the separation solvent (stream 4) of that same patent.

For a base hydrolysis of the solution, care must be taken to choose a proper basic solution that will react with all of the metal compounds. If the metal compounds to be removed are titanium compounds, then titanium hydroxides will precipitate as solids in the basic solution. Therefore, the basic solution should be more dense than the organic phase, so that the basic solution may pass through the organic phase and form a heavier liquid portion at the bottom of the reactor vessel. The solid precipitates will then settle into the basic solution at the bottom portion of the reactor. The substantially metal-free organic phase may then be removed from the upper portion of the reactor and further purified as needed. A primary advantage of the base hydrolysis is that the bottom phase of the reactor, which contains the solid precipitate, may be removed and disposed of with little or no additional treatment.

Vanadium hydroxides, on the other hand, are generally soluble in aqueous base solutions. Thus, vanadium compounds will form in the basic solution, but will not enjoy the additional advantage of forming solid precipitates. If vanadium compounds are removed using the present method, then the basic phase must be further treated to remove solid vanadium for disposal.

The primary concern in preparing the basic solution in cases where solids are formed is that it should be more dense than the liquid hydrocarbon being treated. The basic solution should also contain an excess of the stoichiometric amount of hydroxide necessary to react with all of the heavy metal contained in the treatment solution. The basic solution should be sufficiently dilute so that solid compounds form a slurry that can be easily removed from the bottom portion of the hydrolysis reaction vessel. The desired solids content of the slurry will be dependent upon the equipment used to pump the slurry from the reactor.

In treating a solution of titanium compounds dissolved in a halohydrocarbon, an aqueous solution containing 4% to 25% of a mineral base has been found to be effective. Sodium hydroxide is preferred, but potassium hydroxide or other mineral bases may also be used. The precise amount of sodium or potassium hydroxide contained in the base solution will depend upon the amount of titanium compounds contained in the hydrocarbon and the density of the hydrocarbon. As stated above, the aqueous content of the basic solution is primarily driven by the desired density of the basic titanium slurry product.

In a laboratory-scale confirmation of the concept, 100 mls of material such as found in stream 22 of U.S. Pat. No. 5,242,549 was slowly added to 100 mls of 20% wt. sodium hydroxide solution. The titanium compounds were successfully precipitated into the more dense caustic phase as white solids, and an easily separable organic phase was formed. The organic phase was then recovered and distilled to produce material of sufficient purity to be used as separation solvent in the separation process of the above-described patent.

If an acid hydrolysis is used, different factors will determine the desired composition of the acid solution. In acid hydrolysis, the metal compounds will be soluble in the acid phase of the vessel if a sufficient pH (typically<1) is maintained to prevent the formation of solids. In contrast to the basic hydrolysis, the acid solution does not need to be more dense than the organic phase because there is no concern for solids forming in the bottom portion of the reactor vessel. However, the density of the acid solution should be sufficiently different from the organic phase so that two phases clearly form during the hydrolysis reaction. The preferred acidic solutions are mineral acids such as HCl or $H_2SO_4$. Following hydrolysis, the bottom and top liquid portions of the reactor vessel can be removed separately. Typically, the acid solution will have to be neutralized prior to discharge and metal solids will form which may be separated and disposed of. The substantially metal-free hydrocarbon liquid will be further distilled and purified in the same manner as if the basic hydrolysis were utilized.

While changes in the sequence of steps and in the components of the invention herein described may be made by those skilled in the art, such changes are included in the spirit of this invention as defined by the appended claims.

What is claimed is:

1. A method for removing titanium or vanadium alkoxide compounds from liquid hydrocarbon, wherein the hydrocarbon may be a halohydrocarbon, mixtures comprising: treating the hydrocarbon mixture with an aqueous base solution having a density higher than the density of the hydrocarbon mixture, whereby an upper phase comprising a substantially metal-free liquid hydrocarbon and a lower phase comprising the aqueous base solution and heavy metal hydroxide are formed; and separating said lower phase from said upper phase.

2. The method of claim 1 further comprising purifying the liquid hydrocarbon phase.

3. The method of claim 1 wherein the alkoxide compound is a titanium alkoxide.

4. The method of claim 1 wherein the alkoxide compound is a vanadium alkoxide.

5. The method of claim 2 wherein the liquid hydrocarbon is a haloaromatic hydrocarbon.

6. The method of claim 5 wherein the liquid haloaromatic hydrocarbon is dichlorobenzene or chlorotoluene.

7. The method of claim 2 wherein the liquid hydrocarbon is xylene.

8. A method for removing titanium or vanadium alkoxide compounds from liquid hydrocarbon, which may be a halogenated hydrocarbon, mixture comprising:

treating the hydrocarbon mixture with an acidic solution while maintaining the pH of said solution sufficiently low to form two liquid phases, the first phase comprising a substantially metal-free liquid hydrocarbon and the second phase comprising the titanium or vanadium dissolved into the acidic solution; and separating the two liquid phases from each other and recovering the hydrocarbon phase.

9. The method of claim 8 further comprising purifying the liquid hydrocarbon phase.

10. The method of claim 8 wherein the alkoxide compound is a titanium alkoxide.

11. The method of claim 8 wherein the alkoxide compound is a vanadium alkoxide.

12. The method of claim 9 wherein the liquid hydrocarbon is a haloaromatic hydrocarbon.

13. The method of claim 12 wherein the haloaromatic hydrocarbon is dichlorobenzene or chlorotoluene.

14. The method of claim 9 wherein the liquid hydrocarbon is xylene.

* * * * *